United States Patent [19]

Rasnick

[11] Patent Number: 4,518,528

[45] Date of Patent: May 21, 1985

[54] α AMINO FLUORO KETONES

[76] Inventor: David W. Rasnick, 2508 Magnolia Trail, Sunol, Calif. 94586

[21] Appl. No.: 577,068

[22] Filed: Feb. 6, 1984

Related U.S. Application Data

[63] Continuation-in-part of Ser. No. 496,227, May 19, 1983, abandoned.

[51] Int. Cl.$^3$ ............................................. C07C 103/52
[52] U.S. Cl. .............................................. 260/112.5 R
[58] Field of Search ................................. 260/112.5 R

[56]  References Cited

U.S. PATENT DOCUMENTS 4,153,688  5/1979  Dimicoli et al. .............. 260/112.5 R
4,438,270  3/1984  Bey et al. ..................... 260/112.5 R

OTHER PUBLICATIONS

Chem. Abstr., vol. 101, (1984), 7625v.
Chem. Abstr., vol. 100, (1984), 139590u.
Chem. Abstr., vol. 99, 49361b, (1983).
Chem. Abstr., vol. 97, 446c, (1982).
The Journal of Biological Chemistry 257, (1982), 10063-10068.
Biochimica et Biophysica Acta 485, (1977), 156-166.
Biochimica et Biophysica Acta 755, (1983), 151-154.
J. Mol. Biol., (1980), 139, 423-438.
Journal of Pharmaceutical Sciences, vol. 68, No. 6, Jun. (1979), 696-698.
Biochemistry, vol. 16, No. 13, (1977), 2942-2948.

*Primary Examiner*—Delbert R. Phillips

[57]  ABSTRACT

Novel α amino fluoro ketones, a method of their synthesis and a method for irreversibly inhibiting proteases is disclosed.

12 Claims, No Drawings

α AMINO FLUORO KETONES

This is a continuation-in-part of co-pending patent application filed May 19, 1983 in the United States Patent and Trademark Office, having a Ser. No. 496,227 now abandoned.

This invention relates generally to fluoro ketones, and more particularly to αamino fluoro ketones.

Proteases are a significant class of enzymes and have been associated with a number of diseases including, but not limited to pulmonary emphysema; Mitmen, C. editor (1972) *Pulmonary Emphysema and Proteolysis*, Academic Press, New York, NY: Turino, G. M., Rodriguez, J. R. Greenbaum, L. M., and Mandl, I. (1974) *Am. J. Med.* 57, 493; and Hance, A. J., and Crystal, R. G. (1975) *Am. R. Resp. Disease* 112, 657. Leukocyte elastase is believed to be responsible for most of the tissue destruction in emphysema. Different proteases have been associated with the same or similar disorder. Another protease, cathepsin G is present in the lug and has the ability to digest elastin fibrils.

Protease inhibitors (both naturally occurring and synthetic) act on the reactive site of a protease to inhibit its activity of the enzyme.

In recent years investigators have reported the syntheses of a number of synthetic inhibitors. Peptide chloromethyl ketones (αamino chloromethyl ketones) have been synthetized and it has been descovered that some of these compounds inhibit porcine pancreatic elastase, cathepsin G and human leukocyte elastase. Thompson, R. C., and Blout, E. R. (1973) *Biochemistry* 12, 44; Thompson, R. C. (1973) *Biochemistry* 12, 47;1 Powers, J. C. Gupton, B. F., Harley, A. D., Nishino, N. and Witley, R. J. (1977) *Biochem. Biophys. Acta.* 525, 156; Lively, M. O., and Powers, J. C. (1978) *Biochem. Biophys. Acta.* 525, 171; Yoshimura, T., Barber, L. N., and Powers, J. C. (1982), *J. Biol. Chem.* 257, 5077; and Teshima, T., Griffin, J. C., and Powers, J. C. (1982) *J. Biol. Chem.* 257, 5085.

αAmino chloromethyl ketones have also been synthesized and used to study the physiological and pathological roles of elastases. Janoff, A., Blondin, J., Sandhaus, R. A., Mosser, A., and Malemud, C. (1975) *Proteases and Biological Control* (Reich, E., Rifkin, D. B., and Shaw, E., Editors), pages 603-620, Cold Spring Harbor Laboratory, New York, N.Y.

As inhibitors the αamino chloromethyl ketones have shown a lack of promise in the treatment of disease. They are strongly electrophylic and indiscriminately alkylate non-target molecules present under in vivo conditions.

It would be highly desirable to provide inhibitors which do not produce this indiscriminate akylation. It has been hypothesized that fluoro ketones would possess the desired reduced alkylating potential. A discussion on the ratio of F/Cl rates of reactivity in various displacement reactions is found in Hudlicky, M. (1971) *Organic Fluorine Chemistry*, Plenum Press, New york, NY.

Attempts to synthesize αamino fluoro ketones have proven to be unsuccessful, Powers, J. C. (1977) *Chemistry and Biochemistry of Amino Acids, Peptides and Proteins* (Weinstein, B., Editor), Vol. 4, pages 65-178, Marcel Dekker, New York, N.Y.

Such synthetic methods have generally employed traditional substitutional reactions where the Cl is replaced by F on an αamino chloromethyl ketone. The result has been the destruction of the amine or peptide moiety. In one synthetic method, an attempt was made to substitute the Cl with F on a peptide chloromethyl ketone with the use of KF and 18-Crown-6 ether, Aldrich Chemical Company, Milwaukee, Wis.; a slight excess of KF was employed and the solution refluxed from 10-12 hours. Substitution did not result.

In the synthesis of αamino chloromethyl ketones, an amino diazomethyl ketone is treated with HCl to synthesize the desired end product. Attempts to synthesize amino fluoromethyl ketones by this method (substituting HF for HCl) have proven to be unsuccessful.

Thus, the existence of peptide αamino fluoro ketones has been unknown to date. It would, however, be an advancement in the art to provide such a class of compounds.

SUMMARY OF THE INVENTION

Accordingly, it is an object of the invention to provide a new class of compounds, αamino fluoro ketones.

Another object of the invention is to provide αamino fluoromethyl ketones.

Yet another object of the invention is to provide αamino fluoro ketones having a single amino acid or peptide chain of from 1-6 amino acids.

A further object of the invention is to provide a method of synthesizing αamino fluoro ketones.

Another object of the invention is to provide a method for irreversibly inhibiting serine or cysteine proteases.

Still a further object of the invention is to provide a method for irreversibly inhibiting serine proteases.

To achieve the foregoing and other objects, in accordance with the purpose of the present invention embodied and broadly described herein, the αamino fluoro ketones of the present invention have the formulae:

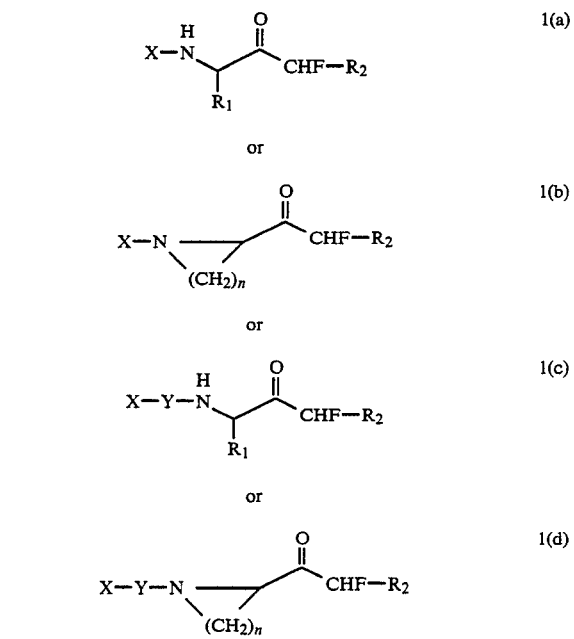

wherein $R_1$ and $R_2$ are independently selected from the group hydrogen, alkyl of 1 to 6 carbons; substituted alkyl of 1-6 carbons; aryl; alkylaryl where the alkyl group is of 1-4 carbons; n is an integer from 1-4 inclusive; X is a peptide end-blocking group; and Y is an amino acid or peptide chain of from 1–6 amino acids.

In another aspect of the present invention, αamino fluoro ketones represented by formulas 1(a)–(d) above are synthesized by suspending an N-acylamino acid or a peptide derivative thereof with about two equivalents of fluoroacetic anhydride in an inert solvent. The solvent is added in an amount equal to about the weight of the N-acylamino acid or peptide derivative. A tertiary amine is then added in an amount of about two equivalents of the N-acylamino acid or peptide derivative and cooled to a temperature of about 0° C. Thereafter, a catalytic amount of a substituted 4-Dialkylaminopyridine catalyst is added and the ketone synthesized.

In a further aspect of the present invention, the method for inhibiting a protease comprises contacting a protease containing analyte, under protease inhibiting conditions, with a compound of formula 1(a), 1(b), 1(c) or 1(d) above, in an amount sufficient to inhibit the protease.

The αamino fluoro ketones of the present invention irreversibly inhibit cysteine and serine proteases. These ketones are not strongly electrophylic and hence do not indiscriminately alkylate non-target molecules under in vivo or in vitro conditions. The αamino fluoro ketones of the present invention are applicable to the preparation of protease inhibitors having therapeutic value. More particularly, αamino fluoro ketones are useful in inhibiting serine and cysteine proteases including but not limited to cathepsins B, H, C, G, R; elastase; trypsin; plasma kallikrein; glandular kallikrein; plasmin; plasminogen activator; and the like.

DETAILED DESCRIPTION OF THE INVENTION

The present invention provides novel αamino fluoro ketones, a method of their synthesis, and a method of irreversibly inhibiting proteases. Inhibition is defined herein as the initial binding of the inhibitors (αamino fluoro ketone) to the recognition site of the protease followed by irreversible covalent bonding of the αfluoromethyl ketone to the active site of the enzyme.

Table I defines the abbreviations used throughout this disclosure.

TABLE I

| | |
|---|---|
| AFC— | aminofluorocoumarin |
| Ala— | alanine |
| Arg— | arginine |
| Amino Acid CH2F— | α amino-acid-fluoro ketone |
| Asp— | aspartic acid |
| Bz— | benzoyl |
| Boc— | t-butoxycarbonyl |
| Bzl— | benzyl |
| Boc—ProCHFCO2—t-butyl- | 2-(2'-t-butoxycarbonyl-2'-fluoroacetyl)-N—t-butoxycarbonylpyrrolidine |
| CHN2— | diazomethyl ketone |
| Cys— | cysteine |
| CO2—t-butyl- | t-butoxycarbonyl |
| CO2—Et— | ethoxycarbonyl |
| Gly— | glycine |
| Leu— | leucine |
| Lys— | lysine |
| MeOSuc— | methoxysuccinyl |
| Pro— | proline |
| Pip— | pipecolic acid |
| Phe— | phenylalanine |
| Ph— | phenyl |
| Ser— | serine |
| Tos— | tosyl |

TABLE I-continued

| | |
|---|---|
| Z— | carbobenzoxy |

The αamino fluoro ketones of the present invention have the structural formulae:

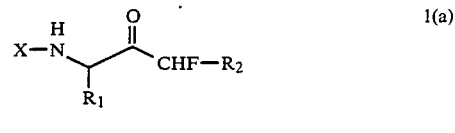

1(a)

or

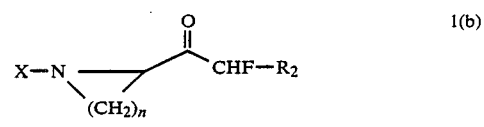

1(b)

or

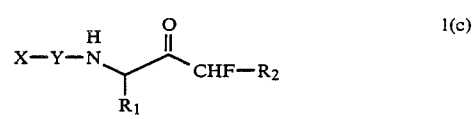

1(c)

or

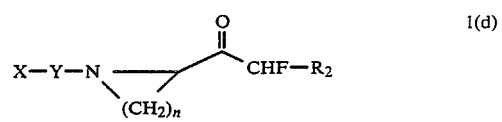

1(d)

Wherein $R_1$ and $R_2$ are independently selected from the group hydrogen; alkyl of 1–6 carbons; substituted alkyl of 1–6 carbons; aryl; alkylaryl where the alkyl group is of 1–4 carbons; n is an integer from 1–4 inclusive; X is a peptide end-blocking group; and Y is an amino acid or peptide chain of from 1–6 amino acids.

Substituted alkyl as used herein is defined as a hydroxy, amino, guanidino, carboxy or mercapto group attached to an alkyl of from 1–6 carbons.

Suitable peptide end-blocking groups (X), (peptide protecting groups) are those well known in the art. As defined herein, a peptide end blocking group is attached to either an amino acid or peptide chain. A listing of suitable peptide end-blocking groups is found in *The Peptides, Synthesis, Biology* (Gross, E. and Meienhofer, J., Editors) Vol. 3 (1981), Academic Press, New York, N.Y.

X is preferably acetyl; benzoyl; carbobenzoxy, glutaryl, t-butoxycarbonyl; succinyl; methoxysuccinyl; D-Pro; D-Val; D-Ala; D-Phe.

More preferably, X is selected from the group benzoyl; t-butoxycarbonyl; methoxysuccinyl; or carbobenzoxy.

$R_2$ is preferably hydrogen.

Y is preferably an amino acid or peptide chain of from 1–4 amino acids.

Of the above formulae 1(c) and 1(d) are preferred.

The αamino fluoro ketones of the present invention are synthesized by the formation of a C—C bond and are not synthesized by the formation of a C—F bond.

In one embodiment, αamino fluoro ketones of formulae 1(a)–(d) above are synthesized by suspending an N-acylamino acid or peptide derivative thereof with about 2 molar equivalents of fluoroacetic anhydride in an amount of an inert solvent of about equal weight to the weight of the N-acylamino acid or peptide derivative. Suitable solvents include but are not limited to benzene, toluene, tetrahydrofuran, dioxane, chloroform, dichloromethane, ethyl acetate, and the like. The preferred solvent is benzene. Two equivalents of a tertiary amine is then added to effect solution while cooled to about 0° C. to control the rate of oxazolone formation. Exemplary tertiary amines include but are not limited to triethylamine, N-methylmopholine, triethylenediamine, and the like. The preferred is triethylamine. A catalytic amount of a 4-Dialkylaminopyridine catalyst is added and then cooling ceased. Exemplary 4-Dialkylaminopyridines include but are not limited to 4-Dimethylaminopyridine and 4-pyrrolidinopyridine. 4-Dimethylamino pyridine is preferred. Vigorous $CO_2$ evolution begins. The resulting solution is stirred for about two hours at room temperature and then diluted about 10 fold by the addition of a water immisible solvent. Exemplary solvents include but are not limited to benzene, toluene, chloroform, dichloromethane, ethyl acetate, and the like. The preferred solvent is benzene. The organic solution formed is washed with dilute acid followed by dilute base wash and saturated NaCl, followed by drying, e.g., over $MgSO_4$, to separate the αamino fluoro ketone from any impurity. Solvent is removed by evaporation and the αamino fluoro ketone purified.

αAmino fluoro ketones of formulas 1(a) and 1(b) above are additionally synthesized by reacting the enolate of tert-butyl fluoroacetate or benzylfluoroacetate with an activated N-urethane protected amino acid in a non-nucleophilic solvent at about $-10°$ to $0°$ C. for about one hour. Activated amino acid is defined herein as an acylating reagent. The reaction mixture is decomposed by treatment with dilute acid at about 0° and then extracted with a water immiscible solvent, washed with dilute base followed by water wash. The resulting organic solution is dried, solvent removed by evaporation and the αamino fluor ketone purified. The ketones prepared by the method can be precursors for the αamino fluoro ketones having formulas 1(c) and 1(d) above.

Preferred enolates include but are not limited to the enolate derivatives of tertiarylentyl fluoroacetate and benzyl fluoro acetate. Enolates are conventionally prepared in inert solvents by treatment with a strong base such as potassium tertiarybutoxide and sodium hydride. Preferred procedures for activating the amino acid include but are not limited to the mixed carbonic anhydride methods, symmetrical anhydride method, carbodiamide method, carbonyldimidiazole method and the like.

The αamino fluoro ketones of the present invention are useful for the irreversible inhibition of cysteine and serine proteases. Exemplary proteases include but are not limited to cathepsins B, H, L, G, R; elastase; trypsin; plasma kallikrein; glandular kallikrein; plasmin; plasminogen activator; and the like.

αAmino fluoro ketones of the present invention when contacted under in vitro inhibition conditions form a covalent bond between the inhibitor and the protease by nucleophilic displacement of the fluorine. The covalent bond formed is at the active site of the protease. A reversible enzyme-inhibitor complex forms at the enzyme active site prior to covalent inactivation of the protease. In each case, the active site of the protease is alkylated.

Each cysteine and serine protease has a different geometry but the reactive site of the protease (alkylated by the inhibitor) is essentially the same. It is at this protease reactive site where displacement of the F of the αamino fluoro ketone occurs. The ketones of the present invention can be of a single amino acid or a peptide chain. Thus, the geometry of the ketone distinguishes it so that it is able to fit the geometry of the protease. However, the reactive sites of the ketones and proteases remain the same in every case.

The method for inhibiting cysteine or serine proteases of the present invention comprises contacting an αamino fluoro ketone of formulae 1(a)–(d) above with a protease under protease inhibiting conditions in an amount sufficient to inhibit the protease at its reactive site. Protease inhibiting conditions are pH of from about 4–10, preferably from about 6–9, most preferably about 6–8; and incubation of the protease and αamino fluoro ketone at a temperature of about 20°–37° C., preferably at about 25° C., with the relative concentrations ranging from about one equivalent of αamino fluoro ketone to one equivalent of protease to about a 60/1 ratio, respectively. The relative amount of ketone inhibitor to protease is dependent on the amount of time desired for inhibition to occur, as well as the particular protease/ketone combination. The protease can be in purified form, in an analyte or in a sample of homogenized tissue.

The following examples illustrate various embodiments of the present invention. They are not intended to limit the scope of the invention which is defined in the claims appended hereto.

Table II summarizes the substituents of αamino fluoro ketones synthesized in Examples 1–19, according to formulae 1(a)–(d) above.

TABLE II

| Compound | X | Y | n | $R_1$ | $R_2$ |
|---|---|---|---|---|---|
| 1. Bz—AlaCH$_2$F | Bz | | | methyl | H |
| 2. Z—Phe—AlaCH$_2$F | Z | Phe | | methyl | H |
| 3. Boc—ProCHFCO$_2$Et | Boc | | 3 | | CO$_2$Et |
| 4. MeOSuc—Phe—Ala—Ala—Phe—Phe—Val—LeuCH$_2$F | MeOSuc | Phe—Ala—Ala—Phe—Phe—Val | | isobutyl | H |
| 5. HCL.ProCH$_2$F | H | | 3 | | H |
| 6. Boc—AlaCHFCO$_2$—t-butyl | Boc | | | | CO$_2$—t-butyl |
| 7. TFA—L-AlaCH$_2$F | H | | | methyl | H |
| 8. MeOSuc—Ala—Ala—Pro—AlaCH$_2$F | MeOSuc | Ala—Ala—Pro | | methyl | H |
| 9. Z—Ala—PheCH$_2$F | Z | Ala | | benzyl | H |
| 10. Z—Phe—LeuCH$_2$F | Z | Phe | | isobutyl | H |
| 11. Boc—Gly—AspCH$_2$F | Z | Gly | | carboxymethyl | H |
| 12. Boc—D-Val—Leu—ArgCH$_2$F | Boc | D-Val—Leu | | 3 quanidinopropyl | |
| 13. Boc—Pro—NHCH(C$_6$H$_{11}$)COCH$_2$F | Boc | Pro | | cyclohexyl | H |
| 14. MeOSuc—Gly—NHCH(C$_6$H$_5$)COCH$_2$F | MeOSuc | Gly | | phenyl | H |
| 15. Z—Ala—NHCH(CH$_2$CH$_2$CH$_2$CH$_2$C$_6$H$_5$)COCH$_2$F | Z | Ala | | 4-phenylbutyl | H |
| 16. Z—Gly—PipCHFCO$_2$Et | Z | Gly | 4 | | CO$_2$Et |

TABLE II-continued

| Compound | X | Y | n | R₁ | R₂ |
|---|---|---|---|---|---|
| 17. Boc—Gly—PheCHFCH₂CH₂CH₂CH(CH₃)₂ | Boc | Gly | | benzyl | 4-methylpentyl |
| 18. Z—Phe—AlaCHFC₆H₅ | Z | Phe | | methyl | phenyl |
| 19. Z—Gly—LeuCHFCH₂CH₂CH₂CH₂C₆H₅ | Z | Gly | | isobutyl | 4-phenylbutyl |
| 20. Z—Ala—GlyCHFCH₂CH(CH₃)₂ | Z | Ala | | H | isobutyl |
| 21. Boc—ProCHFCO₂-t-butyl | Boc | | 3 | | CO₂—t-butyl |

EXAMPLE 1

Synthesis of Bz-AlaCH₂F 3-(N-Benzoylamino)-1-fluoro-2-butanone

N-Benzoylalanine (8.25 grams, 42.8 m mol) and fluoroacetic anhydride (11.8 grams, 85.6 m mol) were combined and treated with 10 milliliters of benzene. Solution was effected by the addition of triethylamine (11.9 ml, 85.6 m mol) and cooled in an ice bath. 4-Dimethylaminopyridine (0.26 grams, 2.15 m mol) was added and the ice bath removed. Vigorous CO₂ evolution began immediately. The solution was stirred two hours at room temperature. Benzene (100 ml) was added. The organic solution was washed with 1N HCl (2×50 ml), saturated NaHCO₃ (2×50 ml), followed by drying over anhydrous MgSO₄. The solvent was removed by evaporation and the resulting oil was applied to a 2.5×80 cm column of silica gel (60 mesh). The BzAlaCH₂F was eluted with chloroform. The chloroform was evaporated off and the residue triturated with petroleum ether to give a solid which melted at 67° to 69° C.

The ¹H nmr (CDCl₃) showed peaks shifted from TMS by δ 1.51 (3H, d, —CH₃), 5.07 (2H, d, $J_{HF}$=47.4 Hz, —CH₂F), 5.09 (1H, m, —CH—), 6.88 (1H, broad s, NH), 7.52 (3H, m, aromatic), 7.74 (2H, m, aromatic). The ¹³C nmr (CDCl₃) showed peaks shifted from TMS by

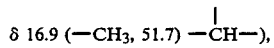
δ 16.9 (—CH₃, 51.7) —CH—), 83.7 (—CH₂F $J_{CF}$=184.3 Hz), 127.2 (aromatic), 128.6 (aromatic), 130.2 (aromatic), 132.1 (aromatic).

The ¹⁹F nmr (CDCl₃) without reference showed a triplet with $J_{HF}$=47.4 Hz. The IR (KBr pellet) showed absorption peaks at 1751 (ketone carbonyl) and 1632 cm⁻¹ (amide carbonyl). Anal. calculated for C₁₁H₁₂FNO₂: C, 63.15; H, 5.78; N, 6.69; F, 9.08. Found: C, 62.42; H, 5.80; N, 6.52; F, 9.37.

EXAMPLE 2

Synthesis of (Z-Phe-AlaCH₂F)

3-(N-Benzyloxycarbonylphenylalanylamido)-1-fluoro-2-butanone

N-Benzyloxycarbonylphenylalanyl-alanine (3.0 g, 8.11 m mol) and fluoroacetic anhydride (2.24 g, 16,22 m mol) were combined and treated with benzene (30 ml). Solution was effected by the addition of triethylamine (1.64 ml, 16.22 m mol) at room temperature. 4-Dimethylaminopyridine (50 mg, 0.41 m mol) was added. The solution was stirred 2 hours at room temperature. Benzene (100 ml) was added. The organic solution was washed with 1N HCl (2×50 ml), saturated NaHCO₃ (2×50 ml), saturated NaCl (2×50 ml) followed by drying over anhydrous MgSO₄. The solvent was removed by evaporation and the residue was applied to a 2.5×60 cm column of silica gel (60 mesh). The Z-Phe-AlaCH₂F was eluted with 2 percent methanol in chloroform. The solvent was evaporated and the residue was crystallized from ether to give 0.24 g, mp 129°–131°.

The ¹H nmr (CDCl₃) showed peaks shifted from TMS by

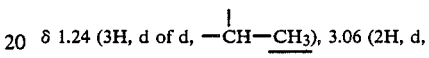
δ 1.24 (3H, d of d, —CH—CH₃), 3.06 (2H, d,

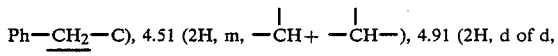
Ph—CH₂—C), 4.51 (2H, m, —CH+ —CH—), 4.91 (2H, d of d,

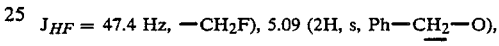
$J_{HF}$ = 47.4 Hz, —CH₂F), 5.09 (2H, s, Ph—CH₂—O),

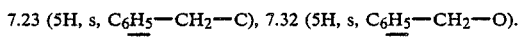
7.23 (5H, s, C₆H₅—CH₂—C), 7.32 (5H, s, C₆H₅—CH₂—O).

The ¹³C nmr (CDCl₃) showed peaks shifted from TMS by

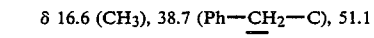
δ 16.6 (CH₃), 38.7 (Ph—CH₂—C), 51.1

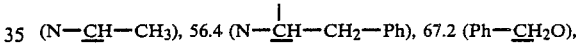
(N—CH—CH₃), 56.4 (N—CH—CH₂—Ph), 67.2 (Ph—CH₂O),

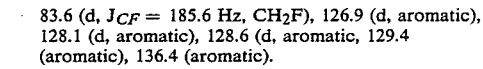
83.6 (d, $J_{CF}$ = 185.6 Hz, CH₂F), 126.9 (d, aromatic), 128.1 (d, aromatic), 128.6 (d, aromatic, 129.4 (aromatic), 136.4 (aromatic).

EXAMPLE 3

Synthesis of (Boc-ProCHFCO₂Et)

2-(2'-Ethoxycarbonyl-2'-fluoroacetyl)-N-t-butoxycarbonylpyrrolidine

Ethyl fluoroacetate (2.0 g, 18.9 m mol) in ether (25 ml) was added dropwise with stirring to a suspension of NaH (50 percent oil dispersion)(0.91 g, 18.9 m mol) in ether (20 ml). The reaction mixture was stirred three hours at room temperature, then cooled to −15°. The mixed anhydride of Boc-Pro-OH [prepared from Boc-Pro-OH (4.1 g, 18.9 m mol) in the THF (50 ml) containing N-methylmorpholine (2.1 ml, 18.9 m mol) at −15°, by the addition of isobutylchloroformate (2.45 ml, 18.9 m mol) and stirred 5 minutes] was filtered into the chilled enolate suspension and stirred at −15° for 10 minutes. The reaction was then allowed to warm to room temperature for one hour. The solution was poured onto ice containing 2.5N H₂SO₄. The organic solvents were removed by evaporation and the aqueous residue extracted with ethyl acetate. The ethyl acetate solution was washed with saturated NaHCO₃, saturated with NaCl, and dried over anhydrous MgSO₄. The ethyl acetate was removed by evaporation and the residue was applied to a silica gel column. The product was eluted with chloroform. The solvent was removed by evaporation yielding 1.08 g of an oil. The ¹H nmr (CDCl₃) showed peaks shifted from TMS by δ 1.45 (12H, m, —C(C$\underline{H}$₃)₃ + —C$\underline{H}$₂CH₃), 2.05 (4H, m,

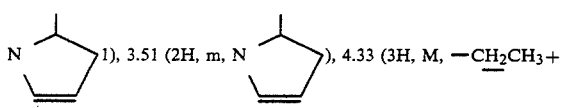 3.51 (2H, m, N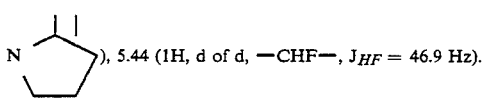), 4.33 (3H, M, —CH₂C$\underline{H}$₃+

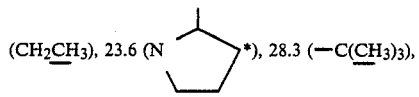, 5.44 (1H, d of d, —CHF—, $J_{HF}$ = 46.9 Hz).

The ¹³C nmr (CDCl₃) showed peaks shifted from TMS by δ 14.1

(C$\underline{H}$₂CH₃), 23.6 (N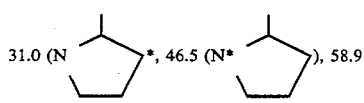*), 28.3 (—C(C$\underline{H}$₃)₃), 31.0 (N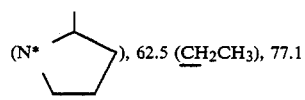*, 46.5 (N*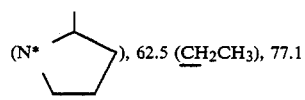), 58.9

(N*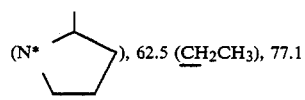), 62.5 (C$\underline{H}$₂CH₃), 77.1

(d, $J_{CF}$ = 168.5 Hz, —CHF—).

EXAMPLE 4

Synthesis of MeOSuc-Phe-Ala-Ala-Phe-Phe-Val-LeuCH₂F

3(N-Methoxysuccinylphenylalanylalanylalanyl-phenylalanylphenylalanylvalylamido)-1-fluoro-5-methyl-2-hexanone To MeOSuc-Phe-Ala-Ala-Phe-Phe-OH (0.82 g 1.14 mM) in tetrahydrofuran (10 ml) containing N-methylmorpholine (0.13 ml, 1.14 m mol) at −10° was added isobutylchloroformate (0.15 ml, 1.14 m mol). The mixture was stirred two minutes at −10°, then a precooled solution of HCl.Val-LeuCH₂F (0.33 g. 1.14 m mol) in dimethylformamide (5 ml) was added followed by N-methylmorpholine (0.13 ml, 1.14 m mol). The mixture was stirred one hour at −10°, then over night at room temperature. The mixture was filtered and the solvents removed by evaporation. The residue was applied to a 2.5×45 cm column of silica gel (60 mesh) and the product eluted with 2 percent methanol in chloroform. The solvent was removed and the residue triturated with ether to give a solid in 24 percent yield.

EXAMPLE 5

Synthesis of HCl.ProCH₂F 2-fluoroacetylpyrrolidine hydrochloride 2-(2'-t-Butoxycarbonyl-2'-fluoroacetyl)-N-t-butoxycarbonylpyrrolidine (1.4 g, 4.2 m mol) was dissolved in dichloromethane (20 ml) and treated with 5.5 N HCl in dioxane (20 ml) at room temperature for one hour. The solution was poured into ether (200 ml). The solid was filtered, washed with ether and pumped dry. The ¹H nmr showed absence of t-butyl groups and retention at 5.22 ($J_{HF}$=47.3 Hz) of the —CH₂F doublet.

EXAMPLE 6

Synthesis of Boc-AlaCHFCO₂-t-butyl 3-(N-t-butoxycarbonyl)-1-fluoro-1-t-butoxycarbonyl-2-butanone To potassium tert-butoxide (1.19 g, 10.6 m mol) in THF (25 ml) at 0° was added dropwise tertbutylfluoroacetate (1.42 g, 10.6 m mol) in 5 ml THF. The ice bath was removed and the yellow solution stirred 20 minutes at room temperature. The solution was then cooled to −10° while the mixed anhydride of Boc-Ala-OH (2 g, 10.6 m mol) was prepared. The mixed anhydride reaction mixture was then filtered into the cooled enolate solution. The resultant solution was stirred one hour at room temperature, after which it was poured onto crushed ice containing 2.5N H₂SO₄. The THF was evaporated and the aqueous residue was extracted with ethyl acetate (2×50 ml). The organic phase was washed with saturated NaHCO₃, and brine, then dried over MgSO₄. The solvent was evaporated and the residue chromatographed on silica gel. The product eluted with 2 percent ethyl acetate in chloroform to give 2.4 g (78 percent) of an oil.

The ¹H nmr (CDCl₃) showed d of d at δ 5.39 (—CHF—, $J_HF$=46.9 Hz).

The ¹³C nmr (CDCl₃) showed d at δ 77.1 (—CHF—, $J_{CF}$=172.1 Hz).

EXAMPLE 7

Synthesis of TFA L-AlaCH₂F

L-1-Fluoro-3-amino-2-butanone trifluoroacetate salt

Boc-AlaCHFCO₂-t-butyl (1 g, 2.46 m mol) was treated with trifluoroacetic acid for twelve hours. The solvent was evaporated and the residue triturcated with ether-petroleum ether to give a solid (0.35 g, 65 percent).

The ¹H nmr (D₂O) showed d at δ 5.48 (—CH₂F, $JH_F$=46.4 Hz).

EXAMPLE 8

Synthesis of MeOSuc-Ala-Ala-Pro-AlaCH₂F 3-(N-Methoxysuccinylalanylalanylprolylamido)-1-fluoro-2-butanone Following the method of Example 1 above, MeOSuc-Ala-Ala-Pro-AlaCH₂F is synthesized by substituting MeOSuc-Ala-Ala-Pro-Ala-OH for N-Benzoylalanine.

EXAMPLE 9

Synthesis of Z-Ala-PheCH₂F 3-(N-benzyloxycarbonylalanylamido)-1-fluoro-3-phenyl-2-butanone Following the method of Example 1 above, Z-Ala-PheCH₂F is synthesized by substituting Z-Ala-Phe-OH for N-Benzoylalanine.

EXAMPLE 10

Synthesis of Z-Phe-LeuCH₂F 3-(N-benzyloxycarbonylphenylalanylamido)-1-fluoro-5-methyl-2-hexanone Following the method of Example 1 above Z-Phe-LeuCH₂F is synthesized by substituting Z-Phe-Leu-OH for N-Benzolylalanine.

EXAMPLE 11

Synthesis of Boc-Gly-AspCH$_2$F 3-(N-t-butoxycarbonylglycylamido)-1-fluoro-4-carboxy-2-butanone Following the method of Example 1 above, Boc-Gly-AspCH$_2$F is synthesized by substituting Boc-Gly-O-BzlAsp-OH for N-Benzoylalanine, followed by catalytic hydrogenation of the resulting Boc-Gly-O-BzlAspCH$_2$F to yield Boc-Gly-AspCH$_2$F.

EXAMPLE 12

Synthesis of Boc-D-Val-Leu-ArgCH$_2$F 3-(N-t-butoxycarbonyl-D-valyl-L-Leucylamido)-1-fluoro-6-guanidino-2-hexanone Following the method of Example 1 above, Boc-D-Val-Leu-ArgCH$_2$F is sythesized by substituting Boc-D-Val-Leu-NO$_2$Arg-OH for N-Benzoylalanine, followed by catalytic hydrogenation of the resulting Boc-D-Val-Leu-(NO$_2$)ArgCH$_2$F to yield Boc-D-Val-LeuArgCH$_2$F.

EXAMPLE 13

Synthesis of Boc-Pro-NHCH(C$_6$H$_{11}$)COCH$_2$F 3-(N-t-butoxycarbonylprolylamido)-1-fluoro-3-cyclohexyl-2-propanone Following the method of Example 1 above, Boc-Pro-NHCH(C$_6$H$_{11}$)COCH$_2$F is synthesized by substituting Boc-Pro-cyclohexyglycine for N-Benzoylalanine.

EXAMPLE 14

Synthesis of MeOSuc-Gly-NHCH(C$_6$H$_5$)COCH$_2$F 3-(N-Methoxysuccinylglycylamido)-1-fluoro-3-phenyl-2-propanone Following the method of Example 1 above, MeOSuc-Gly-NHCH(C$_6$H$_5$)COCH$_2$F is synthesized by substituting MeOSuc-Gly-phenylglycine for N-Benzoylalanine.

EXAMPLE 15

Synthesis of Z-Ala-NHCH(CH$_2$CH$_2$CH$_2$CH$_2$C$_6$H$_5$)-COCH$_2$F 3-(N-benzyloxycarbonylalanylamido)-1-fluoro-7-phenyl-2-heptanone Following the method of Example 1 above, Z-Ala-NHCH(CH$_2$CH$_2$CH$_2$CH$_2$C$_6$H$_5$)-COCH$_2$F is synthesized by substituting Z-Ala-6-phenylnorleucine for N-Benzoylalanine.

EXAMPLE 16

Synthesis of Z-Gly-PipCHFCO$_2$Et 2-(2'-ethoxycarbonyl-2'-fluoroacetyl)-N-(N'-benzyloxycarbonylglycyl piperidine Following the method of Example 3 above, Z-Gly-PipCHFCO$_2$Et is synthesized by substituting Z-Gly-Pipecolic acid for Boc-Pro-OH.

EXAMPLE 17

Synthesis of Boc-Gly-PheCHFCH$_2$CH$_2$CH$_2$CH(CH$_3$)$_2$ 2-(N-t-butoxycarbonylglycylamido)-4-fluoro-8-methyl-1-phenyl-3-nonanone Following the method of Example 1 above, Boc-Gly-PheCHFCH$_2$CH$_2$CH(CH$_3$)$_2$ is synthesized by substituting Boc-Gly-Phe-OH for N-Benzoylalanine and 2-fluoro-6-methylheptanoic anhydride for fluoracetic anhydride.

EXAMPLE 18

Synthesis of Z-Phe-AlaCHFC$_6$H$_5$ 3-(N-benzyloxycarbonylphenylalanylamido)-1-fluoro-1-phenyl-2-butanone Following the method of Example 2 above, Z-Phe-AlaCHFC$_6$H$_5$ is synthesized by substituting 2-fluoro-2-phenylacetic anhydride for fluoroacetic anhydride.

EXAMPLE 19

Synthesis of Z-Gly-LeuCHFCH$_2$CH$_2$CH$_2$CH$_2$C$_6$H$_5$ 7-(N-benzyloxycarbonylglycylamido)-5-fluoro-9-methyl-1-phenyl-6-decanone Following the method of Example 1 above, Z-Gly-LeuCHFCH$_2$CH$_2$CH$_2$CH$_2$C$_6$H$_5$ is synthesized by substituting 2-fluoro-6-phenylhexanoic anhydride for fluoroacetic anhydride and Z-Gly-Leu-OH for N-Benzoylalanine.

EXAMPLE 20

Synthesis of Z-Ala-GlyCHFCH$_2$CH(CH$_3$)$_2$ 1-(N-benzyloxycarbonylalanylamido)-3-fluoro-5-methyl-2-hexanone Following the method of Example 1 above, Z-Ala-GlyCHFCH$_2$CH(CH$_3$)$_2$ is synthesized by substituting Z-Ala-Gly-OH for N-Benzoylalanine and 2-fluoro-4-methylpentanoic anhydride for fluoroacetic anhydride.

EXAMPLE 21

Synthesis of Boc-ProCHFCO$_2$-t-butyl 2-(2'-t-butoxycarbonyl-2'-fluoroacetyl)-N-t-butoxycarbonylpyrrolidine Following the method of Example 3 above, Boc-ProCHFCO$_2$-t-butyl, is synthesized by substituting t-butylfluoroacetate for ethyl fluoroacetate.

EXAMPLE 22

The inhibitory capability of the αamino fluoromethyl ketone Z-Phe-AlaCH$_2$F was evaluated against the known inhibitors Z-Phe-AlaCHN$_2$ and Z-Phe-AlaCH$_2$Cl for its ability to irreversibly inhibit the cysteine protease cathepsin B. Cathepsin B used in the evaluation was isolated and purified from human and rat liver. Enzyme activity was assayed using the synthetic oligopeptide substrate Bz-Val-Lys-Arg-AFC with 10 mM DTT and 1 mM of the activator salt EDTA at pH 6.5 by fluorescence detection of the liberated AFC. Units of enzyme activity were standardized per 100 ml of a 50 percent of glycerol-phosphate buffer solution. A standard concentration of enzyme (10 nM) was preincubated with each inhibitor (50 nM) over set time periods of 3, 5, 10, 15, 20 and 30 minutes, 25°; then all test samples were individually assayed for activity using the same synthetic substrate and condition to determine the remaining units of activity of the purified enzyme. The amount of enzyme activity inhibited by each inhibitor was determined by subtracting the residual activity for each inhibitor against the control activity. The data demonstrated that 0.1 μM Z-Phe-AlaCH$_2$F is an effective inhibitor of purified cathepsin B. The k$_3$ (rate constant of inactivation) for Z-Phe-AlaCH$_2$F was determined to be $9.2 \pm 1.3 \times 10^{-3} s^{-1}$; $K_I$ (inhibitor dissociation constant) was $0.57 \pm 0.09$ μM and $k_3/K_I$ (inhibitor specificity constant) was $16,200 M^{-1} s^{-1}$; (I)=0.40 0.10 μM. For Z-Phe-AlaCHN$_2$, $k_3$ was determined to be $4.1 \pm 1.7 \times 10^{-3} s^{-1}$; $K_I = 7.4 \pm 3.0$ μM; and $k_3/K_I = 546 M^{-1} s^{-1}$; (I)=2.5–0.50 μM. The inhibitor specificity constant ($k_3/K_I$) for Z-Phe-AlaCH$_2$F is 30 fold higher than for Z-Phe-AlaCHN$_2$.

EXAMPLE 23

The inhibitory capability of the αamino fluoromethyl ketone Z-Phe-AlaCH$_2$F was evaluated against the known inhibitor Z-Phe-AlaCH$_2$Cl for its ability to irreversibly inhibit the serine protease elastase from human leukocytes and porcine pancreas. An aqueous solution of elastase (0.3 μM) in 0.1M TES pH 8.2 containing CaCl$_2$ (10 mM) was assayed against the synthetic substrate MeOSuc-Ala-Ala-Pro-Val-MNA. The liberated detecting group (MNA) was quantitated by fluorescence. A standard number of enzyme units were preincubated with each inhibitor at several concentrations for set time periods of 5, 15, 30, and 60 minutes at 37°; then all test samples were individually assayed for activity using the same synthetic substrate and conditions as per control with inhibitors absent. The amount of enzyme activity inhibited by each inhibitor was determined by subtracting the residual activity for each inhibitor against the control activity. The data demonstrated that Z-Phe-AlaCH$_2$F under alkaline conditions inhibits porcine pancreatic elastase.

EXAMPLE 24

Following the method of Example 22 above, the cysteine protease cathepsin L is inhibited by Z-Phe-PheCH$_2$F under the same conditions and concentration of protease to ketone inhibitor.

EXAMPLE 25

Following the method of Example 22, above, the cysteine protease cathepsin L is inhibited by Z-Phe-AlaCH$_3$F under the same conditions and concentrations of protease to ketone inhibitor.

EXAMPLE 26

Following the method of Example 23, above, the serine protease plasminogen activator is inhibited by MeOSuc-Gly-Gly-ArgCH$_2$F under the same conditions with a protease concentration of about 50 μM and a ketone inhibitor concentration of about 0.1 mM.

EXAMPLE 27

Following the method of Example 23, above, the serine protease plasma kallikrein is inhibited by the ketone inhibitor D-Pro-Phe-ArgCH$_2$F under the same conditions with a protease concentration of about 10 μM and ketone inhibitor concentration of about 0.1 mM.

EXAMPLE 28

Following the method of Example 23 above, the serine protease glandular kallikrein is inhibited by the ketone inhibitor D-Val-Leu-ArgCH$_2$F with a protease concentration of about 10 μM and a ketone inhibitor concentration of about 0.1 mM.

EXAMPLE 29

Following the method of Example 23 above, the serine protease trypsin is inhibited by the ketone inhibitor Z-LysCH$_2$F with a protease concentration of about 10 μM and a ketone inhibitor concentration of about 0.1 mM.

EXAMPLE 29

The rate of inhibition of cathepsin B in rat spleen, pancreas, liver and kidney tissue homogenates was assayed using the inhibitors: Z-Phe-AlaCHN$_2$; Z-Phe-AlaCH$_2$Cl; and Z-Phe-AlaCH$_2$F.

The proceding tissues were homogenized, centrifuged at 13,000 rpm for 25 minutes and the supernatant removed. Aliquots of the supernatant were diluted with water to yield a concentration of 0.01 μM. The method of Example 9 was followed. As soon in Table III, the inhibition by the three inhibitors relevant to Cathepsin B were compared for each of the tissue samples. Results are expressed as τ (the half-time of inactivation, inhibition). The lower the half-time, the more potent the inhibitor. The concentration for the inhibitors was 0.10 μM and the incubation temperature was 25°.

TABLE III

| | Inhibitor | τ Half-Time |
|---|---|---|
| SPLEEN | —CHN$_2$ | 26.4 min. |
| | —CH$_2$Cl | 74.2 |
| | —CH$_2$F | 14.2 |
| PANCREAS | —CHN$_2$ | 15.8 |
| | —CH$_2$Cl | 21.4 |
| | —CH$_2$F | 12.4 |
| LIVER | —CHN$_2$ | 22.4 |
| | —CH$_2$Cl | 66.5 |
| | —CH$_2$F | 8.5 |
| KIDNEY | —CHN$_2$ | 20.1 |
| | —CH$_2$Cl | 76.6 |
| | —CH$_2$F | 7.9 |

The foregoing description of preferred embodiments of the invention has been presented for purposes of illustration and description. It is not intended to be exhaustive or to limit the invention to the precise form disclosed, and obviously modifications and variations are possible in light of the above teaching. The embodiments were chosen and described in order to best explain the principles of the invention and their practical applications, to thereby enable others skilled in the art to best utilize the invention in various embodiments and with various modifications as are suited to the particular use contemplated. It is intended that the scope of the invention be defined by the claims appended hereto.

I claim:

1. A composition of matter, comprising an αamino fluoro ketone compound of the structural formulae:

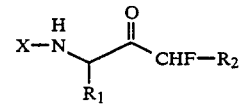

1(a)

or

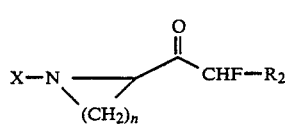

1(b)

or

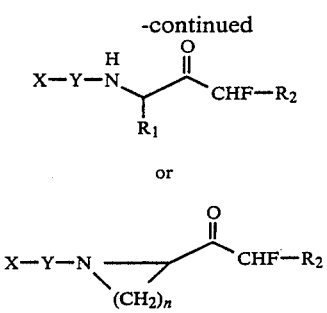

1(c)

$$X-Y-N(CH_2)_n - C(=O) - CHF-R_2$$

1(d)

wherein $R_1$ and $R_2$ are independently selected from the group of hydrogen; alkyl of 1–6 carbons; substituted alkyl of 1–6 carbons; aryl; alkylaryl where the alkyl group is of 1–4 carbons; n is an integer from 1–4 inclusive; X is a peptide end-blocking group; and Y is an amino acid or peptide chain of 1–6 amino acids.

2. The composition of matter according to claim 1, wherein substituted alkyl is a hydroxy, amino, quanidino, carboxy, or mercapto substituent on an alkyl having 1–6 carbons.

3. The composition of matter according to claim 1, wherein X is acetyl, benzoyl, carbobenzoxy, glutaryl, t-butoxycarbonyl, succinyl, methoxysuccinyl, D-Pro, D-Val, D-Leu, or D-Phe.

4. The composition of matter according to claim 1, wherein X is benzoyl, t-butoxycarbonyl, methoxysuccinyl, or carbobenzoxy.

5. The composition of matter according to claim 1 wherein $R_2$ is H.

6. The composition of matter according to claim 1 wherein Y is an amino acid or peptide chain of from 1–4 amino acids.

7. The composition of matter according to claim 1, wherein said compound is Bz-AlaCH$_2$F.

8. The composition of matter according to claim 1, wherein said compound is Z-Phe-AlaCH$_2$F.

9. The composition of matter according to claim 1, wherein said compound is Boc-ProCHFCO$_2$Et.

10. The composition of matter according to claim 1, wherein said compound is Boc-AlaCHFCO$_2$-t-butyl.

11. The composition of matter according to claim 1, wherein said compound is MeOSuc-Ala-Ala-ProAlaCH$_2$F.

12. The composition of matter according to claim 1, wherein said compound is MeOSuc-Phe-Ala-PhePhe-Val-LeuCH$_2$F.

* * * * *